(12) United States Patent
Ansaldi et al.

(10) Patent No.: US 6,620,918 B2
(45) Date of Patent: Sep. 16, 2003

(54) SEPARATION OF POLYPEPTIDE MONOMERS

(75) Inventors: Deborah Ann Ansaldi, San Mateo, CA (US); Philip Lester, San Lorenzo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/320,100

(22) Filed: May 26, 1999

(65) Prior Publication Data

US 2002/0010319 A1 Jan. 24, 2002

Related U.S. Application Data (60) Provisional application No. 60/087,602, filed on Jun. 1, 1998.

(51) Int. Cl.[7] .............................. C07K 1/18; C07K 1/20; C07K 1/22; C07K 1/14
(52) U.S. Cl. ........................ 530/416; 530/412; 530/413; 530/417; 530/418
(58) Field of Search .............................. 530/412, 413, 530/416, 417, 418

(56) References Cited

U.S. PATENT DOCUMENTS

| | | | |
|---|---|---|---|
| 4,228,154 A | | 10/1980 | Fisher et al. |
| 4,764,279 A | * | 8/1988 | Tayot et al. ................. 210/656 |
| 4,765,903 A | * | 8/1988 | D'Andrea et al. ........... 210/635 |
| 5,110,913 A | | 5/1992 | Coan et al. |
| 5,231,178 A | | 7/1993 | Holtz et al. |
| 5,250,663 A | | 10/1993 | Tenold |
| 5,256,294 A | | 10/1993 | Van Reis |
| 5,490,937 A | | 2/1996 | Van Reis |

FOREIGN PATENT DOCUMENTS

| | | |
|---|---|---|
| EP | 452753 | 10/1991 |
| EP | 460426 B1 | 12/1991 |
| JP | 7285885 | 10/1995 |
| WO | WO 92/04970 | 4/1992 |
| WO | 96/40776 | 12/1996 |
| WO | WO 99/57134 | 11/1999 |

OTHER PUBLICATIONS

Yang, J. et al. Molecular Immunology, 32(12): 873–881, 1995.*

Arndt, K.M. et al. Biochemistry 37: 12918–12926, 1998.*

Yang et al., Influence of column type and chromatographic conditions on the ion exchange chromatography of immunoglobulins. Journal of Chromatography, vol. 743, pp 171–180.*

Hahn et al., Bovine whey fractionation based on cation–exchange chromatography, Journal of Chromatography, vol. 795, pp 277–287.*

Harlow et al., "Antibody Molecules" *Antibodies: A Laboratory Manual*, Cold Spring Harbor Laboratory pp. 7, 10 (1988).

Roitt, "Molecules Which Recognize Antigen" *Essential Immunology*, Sixth edition, Blackwell Scientific Publications pp. 31, 40 (1988).

Lemque et al., "Study of the absorption of self–associating proteins on an anion exchanger:. Application to the chromatography of β–lactoglobulin B" *Journal of Chromatography* 599:255–265 (1992).

Chaudhary, V. K., et al., "A recombinant immunotoxin consisting of two antibody variable domains fused to *Pseudomonas exotoxin*" *Nature* 339:394–397 (Jun. 1, 1989).

Jiskoot, W., et al., "Two–step purification of a murine monoclonal antibody intended for therapeutic application in man—Optimisation of purification conditions and scaling up" *J. of Immunological Methods* 124:143–156 (1989).

Lynch, Paul, et al., "System for Aggregate Removal from Affinity–Purified Therapeutic–Grade Antibody" *Genetic Engineering News* 17(19):17 (Nov. 1, 1997).

U.S. patent application Ser. No. 09/304,465, Basey et al., filed May 5, 1999.

Chang et al., "Single–Step Solubilization and Folding of IGF–1 Aggregates from *Escherichia coli*" *Protein Folding: In Vivo and In Vitro*, American Chemical Society, Chapter 14, pp. 178–188 (1993).

Elliott et al., "Yeast–Derived Recombinant Human Insulin–Like Growth Factor I: Production, Purification and Structural Characterization" *J. Protein. Chem.* 9(1):95–104 (1990).

\* cited by examiner

*Primary Examiner*—Anthony C. Caputa
*Assistant Examiner*—Anne L. Holleran
(74) *Attorney, Agent, or Firm*—Janet E. Hasak (57) ABSTRACT

A method is disclosed for separating a polypeptide monomer from a mixture comprising dimers and/or multimers. The method comprises applying the mixture to either a cation-exchange chromatography resin or an anion-exchange chromatography resin and eluting the mixture at a gradient of about 0–1 M of an elution salt, wherein the monomer is separated from the dimers and/or multimers present in the mixture.

15 Claims, 8 Drawing Sheets

SEPARATION OF POLYPEPTIDE MONOMERS

RELATED APPLICATIONS

This application is a non-provisional application filed under 37 CFR 1.53(b)(1), claiming priority under 35 USC 119(e) to provisional application No. 60/087,602 filed Jun. 1, 1998, the contents of which are incorporated herein by reference.

BACKGROUND OF THE INVENTION

1. Field of the Invention

This invention relates to a process for separating polypeptide monomers from dimers and/or other multimers using ion-exchange chromatography.

2. Description of Background and Related Art

Attempts to purify authentic, properly folded protein from recombinant hosts have been frustrated due to the tertiary structure of the molecule. In this regard, purification of the recombinantly produced molecule often yields a heterogeneous mixture that consists largely of inactive, misfolded, insoluble, and/or soluble dimers, multimers, and disulfide-linked aggregates. Other aberrant molecules, such as fragments, nicked, oxidized, and glycosylated forms, may also be present. Thus, purification is difficult and yields of the authentic monomer are often low. See, e.g., Elliott et al, *J. Protein Chem.*, 9: 95–104 (1990).

Different techniques have been used to correct these problems. For example, Chang and Swartz, *Protein Folding: in vivo and in vitro* (American Chemical Society, 1993), pp. 178–188 describe a method for solubilizing aggregated IGF-I produced in *E. coli*, using low concentrations of urea and dithiothreitol (DTT) in an alkaline buffer. U.S. Pat. No. 5,231,178 describes a method for the purification of correctly folded, monomeric IGF-I from *P. pastoris* using a combination of cation exchange, hydrophobic interaction, and gel filtration chromatography. WO 96/40776 describes a method for producing authentic properly folded IGF from yeast using a first cation exchange chromatography with the yeast cell medium, denaturing and chromatography, and performing reverse phase high performance liquid chromatography.

Separation of protein and peptide monomers from their dimers, tetramers, and multimers presents a serious challenge to the separations scientist. Size-exclusion chromatography (SEC) and Tangential-Flow Filtration (TFF) (U.S. Pat. Nos. 5,256,294 and 5,490,937) have been used for separating monomers from aggregates but have limitations. SEC can separate monomers from multimers, and in some cases monomers from dimers. The main limitations of SEC are 1) limited load volumes (typically 5% of the bed volume) requiring large columns or multiple cycles, 2) and load protein concentration (low concentration feed stocks require pre-concentration or multiple cycles on the column. Higher protein concentrations can be more viscous, thereby reducing the efficiency of the separation). Historically TFF can separate protein multimers that are ten-fold larger than the monomer. U.S. Pat. No. 5,256,294.

U.S. Pat. Nos. 4,228,154 and 5,250,663 disclose separations of albumin from mixtures. U.S. Pat. No. 4,228,154 describes use of both cation-exchange and anion-exchange chromatography steps for the purification, without separation of monomer from multimers.

There is a need for separating monomers from dimers and multimers that is satisfactory, requires the use of only one ion-exchange step, and does not have the limitations of SEC or TFF.

SUMMARY OF THE INVENTION

Accordingly, this invention provides a method for separating a polypeptide monomer from a mixture comprising dimers and/or multimers, wherein the method comprises applying the mixture to either a cation-exchange or an anion-exchange chromatography resin in a buffer, wherein if the resin is cation-exchange, the pH of the buffer is about 4–7, and wherein if the resin is anion-exchange, the pH of the buffer is about 6–9, and eluting the mixture at a gradient of about 0–1 M of an elution salt, wherein the monomer is separated from the dimers and/or multimers present in the mixture.

In this study it is demonstrated that ion-exchange chromatography—either anion or cation—is an effective means to separate protein or polypeptide monomers from their dimers and/or multimers. Separations are performed using either step or linear gradient elution. Ion exchange has several advantages over the SEC and TFF methods described above. First, separation is independent of polypeptide concentration in the load and therefore no pre-concentration is required. Second, resins can be loaded to greater than 30 mg polypeptide/mL resin and still achieve excellent separations. Third, ion-exchange resins are inexpensive and easy to use. Typical separations achieve enrichment of monomer to greater than 99.5% purity and yields in excess of 90%.

BRIEF DESCRIPTION OF THE DRAWINGS

FIG. 1A is full-scale; FIG. 1B is a close-up view to show the dimers and multimers.

FIGS. 2A1, 2A2, 2B, and 2C show separation of anti-IgE monoclonal antibody monomer from dimers and multimers. FIGS. 2A1 and 2A2 were run on a RESOURCE Q™ anion-exchange column. FIG. 2A1 is full-scale; FIG. 2A2 is a close-up view to show the dimers and multimers. FIG. 2B is a run on Q-SEPHAROSE FAST-FLOW™ resin. FIG. 2C is a plot of monomer and dimer/multimer observed in fractions, where the open dots are monomer and the solid dots are dimer. The monomer and dimer/multimer were determined using a SUPERDEX 200 HR™ 10/30 analytical size-exclusion column (Pharmacia Biotech). In all cases the columns were equilibrated in 25 mM Tris/pH 8. The gradient used in the FIG. 2A panels was 0 to 0.5 M sodium chloride over 40 column volumes. The gradient used for FIG. 2B (Q-SEPHAROSE FAST-FLOW™) was 0.05 to 0.2 M NaCl over 10 column volumes.

FIGS. 3A–C show separation of BSA monomer and dimer on a RESOURCE Q™ anion-exchange column at pH 8. The column was equilibrated in 25 mM Tris/pH 8, and eluted with a gradient from 0.125 to 0.275 M sodium chloride over 40 column volumes. FIG. 3A is purified monomer, FIG. 3B is purified dimer, and FIG. 3C is a commercial preparation of BSA (Bayer) that contains both monomer and dimer.

FIGS. 4A–C show separation of BSA monomer and dimer on a RESOURCE Q™ anion-exchange column at pH 6. The column was equilibrated in 20 mM sodium phosphate/pH 6, and eluted with a linear gradient from 0 to 0.5 M sodium chloride over 10 column volumes. FIG. 4A is purified monomer, FIG. 4B is purified dimer, and FIG. 4C is a commercial preparation of BSA (Bayer) that contains both monomer and dimer.

FIGS. 5A and 5B show separation of anti-IgE monoclonal antibody monomer from dimers and multimers on a RESOURCE S™ cation-exchange column at pH 6. The column was equilibrated in 20 mM sodium phosphate/pH 6, and eluted with a linear gradient from 0 to 0.05 M sodium chloride over 30 column volumes. FIG. 5A is the chromatogram from the separation, and FIG. 5B is a plot of monomer and dimer/multimer observed in fractions using the same method described in FIG. 2, where the open dots are monomer and the solid dots are dimer.

FIG. 6A is purified monomer, and FIG. 6B is purified dimer.

DETAILED DESCRIPTION OF THE PREFERRED EMBODIMENTS

Definitions

As used herein, "polypeptide" refers generally to peptides and proteins having more than about ten amino acids. Preferably, the polypeptides are "exogenous," meaning that they are "heterologous," i.e., foreign to the host cell being utilized, such as a human protein produced by *E. coli*. However, they may also be derived from a native source in which they are present naturally.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; 1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF; cardiotrophins (cardiac hypertrophy factor) such as cardiotrophin-1(CT-1); platelet-derived growth factor (PDGF); fibroblast growth factor such as aFGF and bFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; serum albumin, such as human serum albumin (HSA) or bovine serum albumin (BSA); colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressing; regulatory proteins; antibodies; and fragments of any of the above-listed polypeptides.

The preferred polypeptides of interest are mammalian polypeptides. Examples of such mammalian polypeptides include enzymes, hormones, cytokines, albumins, chemokines, immunotoxins, viral components, antibodies, neurotrophins, and antigens. Suitable such polypeptides encompass polypeptides such as HSA, BSA, anti-IgE, anti-CD20, anti-IgG, t-PA, gp 120, anti-CD11a, anti-CD18, anti-VEGF, VEGF, TGF-beta, activin, inhibin, anti-HER-2, DNase, IGF-I, IGF-II, brain IGF-I, growth hormone, relaxin chains, growth hormone releasing factor, insulin chains or pro-insulin, NGF, NT-3, BDNF, and urokinase. Particularly preferred mammalian polypeptides include, e.g., t-PA, gp120 (IIIb), anti-HER-2, anti-CD11a, anti-CD18, anti-VEGF, VEGF, BSA, HSA, anti-CD20, anti-IgE, anti-IgG, DNase, IGF-I, IGF-I1, TGF-beta, IGFBP-3, IGFBP-2, IGFBP-1, growth hormone, NGF, NT-3, NT-4, NT-5, and NT-6. The polypeptide is more preferably an antibody or a serum albumin, more preferably, anti-IgE, anti-IgG, anti-Her-2, anti-CD11a, anti-CD18, anti-CD20, anti-VEGF, BSA, or HSA.

For purposes herein, the "mixture" contains monomers and either dimers or multimers or both dimers and multimers. Typically, the mixture is a biological fluid, which denotes any fluid derived from or containing cells, cell components, or cell products. Biological fluids include, but are not limited to, fermentation broth, cell culture supernatants, cell lysates, cleared cell lysates, cell extracts, tissue extracts, blood, plasma, serum, sputum, semen, mucus, milk, and fractions thereof. This definition includes cell-conditioned culture medium, which denotes a nutrient medium in which cells have been cultured and which contains cell products.

For purposes herein, "ion-exchange chromatography resin" refers to chromatography medium for anion- or cation-exchange separation.

As used herein, "elution salt" refers to an alkaline earth, alkali metal, or ammonium salt, i.e., a salt having a cation from the alkaline earth or alkali metal elements or an ammonium cation and having an inorganic or organic (hydrocarbon-based) anion. Examples of such salts include sodium chloride, ammonium chloride, sodium citrate, potassium citrate, potassium chloride, magnesium chloride, calcium chloride, sodium phosphate, calcium phosphate, ammonium phosphate, magnesium phosphate, potassium phosphate, sodium sulfate, ammonium sulfate, potassium sulfate, magnesium sulfate, calcium sulfate, etc. Preferred salts herein are chlorides or sulfates. The most preferred salt herein is sodium chloride.

As used herein, "multimers" refer to n-mers where n is 3–10, i.e., polymers that are not dimers but exclude aggregates. In contrast to multimers, aggregates have a value for n of greater than 10, and/or a molecular weight of greater than 2 million daltons, and/or are species contained in the excluded volume of analytical size-exclusion chromatography columns such as SUPEROSE 6™ (Pharmacia).

Modes for Carrying out the Invention

This invention relates to a method of separating monomers of polypeptides from their dimers or multimers or both. The method involves placing the mixture of monomers and dimers and/or multimers, from whatever source, in an equilibration buffer at a pH in the range of about 4 and 9 depending on whether the resin used for chromatographic separation is a cation- or anion-exchange resin. The resulting mixture is loaded onto either a cation-exchange or anion-exchange chromatography resin to capture all the n-mers (monomers, dimers, trimers, tetramers, etc.) present in the mixture. For ion-exchange column chromatography, ligands of general affinity can be used to achieve the desired selectivities and binding properties. The loading takes place in a buffer at a pH of about 6–9 if the resin is anion-exchange and about 4–7 if the resin is cation-exchange. The exact pH will depend, for example, on the isoelectric point of the polypeptide.

If the resin is a cation-exchange resin, prior to loading the mixture, the matrix can be equilibrated using several column volumes of a dilute, weak acid (e.g., four column volumes of 20 mM acetic acid, pH 3, or of 20 mM phosphoric acid, pH about 2.8). Following equilibration, the mixture is added and the column can be washed one to several times, prior to elution of the mixture, also using a weak acid solution such as a weak acetic acid or phosphoric acid solution. The buffer used for this purpose depends on, e.g., the polypeptide and the anionic or cationic nature of the resin. For anion-exchange, preferably the buffer is TRIS or phosphate buffer; for cation-exchange, the buffer is preferably acetate or phosphate buffer.

Ion-exchange chromatography is typically carried out at a temperature of about 18–25° C., preferably about 20° C. (room temperature). The preferred column loading is about 1 ml resin per 20–30 mg total polypeptide.

Following adsorption of the n-mer molecules to the ion exchanger, the mixture is eluted by contacting the resin with an elution salt having an appropriate ionic strength to displace the monomer from the matrix. An elution salt gradient is used of about 0 to 1 M. The gradient may be linear or stepwise. Preferably the gradient is from about 0 to 500 mM elution salt, more preferably 50 to 200 mM elution salt, and most preferably, 0 to 50 mM elution salt. Preferably the elution salt is a sodium salt, such as sodium chloride, although other elution salts and concentration gradients, known to those of skill in the art, also find use herein. The quantity of elution buffer can vary widely and will generally be in the range of about 2 to 40 column volumes, preferably 10 to 40 column volumes. Following elution, the eluate can be assayed for total monomeric concentration.

Suitable cation-exchange resins herein include a wide variety of materials known in the art, including those capable of binding polypeptides over a wide pH range. For example, carboxymethylated, sulfonated, agarose-based, or polymeric polystyrene/divinyl benzene cation-exchange matrices are particularly preferred. Other useful matrix materials include, but are not limited to, cellulose matrices, such as fibrous, microgranular, and beaded matrices; dextran, polyacrylate, polyvinyl, polystyrene, silica, and polyether matrices; and composites. These matrices include, for example, CM52 CELLULOSE™ (Whatman, Inc.); S-HYPERD™ and CM SPHERODEX™ (Secpracor); SP SEPHAROSE FF™, DEAE SEPHAROSE FF™, CM-SEPHAROSE™, and RESOURCE S™ (Amersham Pharmacia Biotech AB); and JT BAKER CSx™ (J.T. Baker, Inc.), as well as those containing the functional ligand R—SO$_3^-$, preferably sulfopropyl resins, such as TOYOPEARL SP550C™ (Tosohaas) and FRACTOGEL EMD™ SO$_3^-$-650 (m) (Merck). Other suitable materials for use in cation-exchange chromatography are within the knowledge of those skilled in the art.

Anion-exchange chromatography is carried out using media appropriate therefor, as are known in the art. Suitable media include, e.g., polymeric polystyrene/divinyl benzene resins and agarose-based resins, as well as agarose beads, dextran beads, polystyrene beads, media that comprise an insoluble, particulate support derivatized with tertiary or quaternary amino groups., and supports derivatized with trimethylaminoethyl groups. Examples of suitable such media include DE92™ (diethylaminoethyl cellulose, Whatman); DEAE-CELLULOSE™ (Sigma), BAKERBOND ABX 40 mu™ (J.T. Baker, Inc.); DEAE resins such as FRACTOGEL EMD DEAE-650™ (EM Separations), FRACTOGEL EMD TMAE-650 (S)™ (EM Science, Gibbstown, N.J.), TSK gel DEAE-SPW™ (Tosohaas), DEAE-SEPHAROSE CL-6B™ and chelating SEPHAROSE™ (Amersham Pharmacia Biotech AB), DEAE MERE SEP. 1000™ (Millipore), and DEAE SPHERODEX™ (Sepracor); RESOURCE Q™ and Q SEPHAROSE™ (QSFF) (Amersham Pharmacia Biotech AB); MACRO-PEP Q™ (Bio-Rad Laboratories, Hercules, Calif.); Q-HYPERD™ (BioSepra, Inc., Marlborough, Mass.); and the like. Other suitable anion-exchange chromatography materials, as well as the selection and use of these materials for the present application, are conventional in the art.

Purified fractions of monomer obtained from the ion-exchange chromatography may be further processed by subjecting them to any appropriate technique designed for downstream processing and purification. This will depend largely on the type of polypeptide and its intended use. Only one ion-exchange step is necessary to effect the desired separation of monomer from dimers and/or multimers in a mixture, although the invention does not exclude using more such steps if desired in the upstream or downstream processing of the polypeptide.

The invention will be more filly understood by reference to the following examples. They should not, however, be construed as limiting the scope of the invention. All literature and patent citations herein are incorporated by reference.

EXAMPLE I

This example shows the separation of anti-IgE monomers and bovine serum albumin monomers from dimers and multimers.

Materials and Methods

Resins

Pharmacia Q-SEPHAROSE FAST FLOW™. 4 mL to 235L bed volumes evaluated

Pharmacia RESOURCE S and RESOURCE Q™: 1 mL prepacked columns

JT Baker CSx™, 0.46×5 cm, 5$\mu$ particles

Proteins

A. Humanized anti-IgE monoclonal antibodies (IgG$_1$) available from Genentech, Inc.: pI~7.5, designated as E25 and E26. WO 93/04173 published Mar. 4, 1993 describes humanized anti-IgE antibodies wherein a murine antibody directed against human IgE (MaE11) was used to provide the CDR regions that were substituted into an IgG1 immunoglobulin framework (rhuMaE25). See also Cacia et al., *Biochemistry*, 35: 1897–1903 (1996) for studies and further descriptions of E-25.

B. Monoclonal anti-IgE antibody prepared from the culture supernatants of an immortalized human myeloma cell line U266B1 (ATCC TIB 196) using affinity chromatography purification on an isolated anti-IgE antibody (Genentech MAE1). Specifically, five BALB/c female mice, age six weeks, were immunized in their foot pads with 10 $\mu$g of purified IgE in Ribi's adjuvant. Subsequent injections were done in the same manner at one and three weeks after the initial immunizations. Three days after the final injection, the inguinal and popliteal lymph nodes were removed and pooled, and a single cell suspension was made by passing the tissue through steel gauze. The cells were fused at a 4:1 ratio with mouse myeloma P3X63-Ag8.653 (ATCC CRL 1580) in high glucose (DMEM) containing 50% w/v polyethylene glycol 4000. Alternatively, the immunizations were done in a similar manner except that 30 µg of IgE per injection were used and IgE fragment 315–347 (Kabat) was assayed as a prefusion boost; or injections were given subcutaneously in two doses of 100 µg and a final booster of 50 µg, and spleen cells were used for the fusions.

The fused cells were then plated at a density of 2×105 per well in 96-well tissue culture plates. After 24 hours HAT selective medium hypoxanthine/aminopterin/thymidine, Sigma, #H0262) was added. Of 1440 wells plated, 365 contained growing cells after HAT selection.

Fifteen days after the fusion, supernatants were tested for the presence of antibodies specific for human IgE using an enzyme-linked immunosorbent assay (ELISA). The ELISA was performed as follows, with all incubations done at room temperature. Test plates (Nunc Immunoplate) were coated for 2 hours with rat anti-mouse IgG (Boehringer Mannheim, #605-500) at 1 µg/ml in 50 mM sodium carbonate buffer, pH 9.6, then blocked with 0.5% bovine serum albumin in phosphate buffered saline (PBS) for 30 minutes, then washed four times with PBS containing 0.05% TWEEN 20™ (PBST). Test supernatants were added and incubated two hours with shaking, then washed four times with PBST. Human IgE (purified from U266 cells as described above) was added at 0.5 µg/ml and incubated for one hour with shaking, then washed four times in PBST. Horseradish-peroxidase-conjugated goat anti-human IgE (Kirkegarrd & Perry Labs, #14-10-04, 0.5 mg/ml) was added at a 1:2500 dilution and incubated for one hour, then washed four times with PBST. The plates were developed by adding 100 µl/well of a solution containing 10 mg of o-phenylenediamine dihydrochloride (Sigma, #P8287) and 10 µl of a 30% hydrogen peroxide solution in 25 ml phosphate citrate buffer, pH 5.0, and incubating for 15 minutes. The reaction was stopped by adding 100 µl/well of 2.5 M sulfuric acid. Data were obtained by reading the plates in an automated ELISA plate reader at an absorbance of 490 nm. For one antibody, 365 supernatants were tested and 100 were specific for human IgE. Similar frequencies of IgE specificity were obtained when screening for the other antibodies.

C. Bovine serum Albumin: pI 4.7 and 4.9 (Radola, *Biochim. Biophys. Acta,* 295: 412–428 (1973))

Bayer Corp. P/N 81-024-2, "Bovine Albumin, Sulfhydryl Modified" (BSA Mix, blocked)

ICN Biomedical Inc. P/N 810013, "Albumin Bovine" (BSA Mix, native)

BSA monomer and dimer prepared in house from Bayer BSA (BSA Monomer and BSA Dimer, respectively)

Chromatography Systems
Hewlett-Packard1090™ HPLC
Pharmacia™ FPLC
Detection at 215 or 280 nm
Buffers: (see Table I for details)
Purified water
Tris•HCl
Sodium acetate
Sodium chloride
Sodium phosphate
Sodium citrate and citric acid
Sample Preparation Samples were diluted with the buffer used for equilibration (indicated in Table I below) to assure pH and conductivity matched starting column conditions. All samples were 0.2-µm filtered prior to loading.

Chromatography

Samples were introduced to the column using either an automatic or manual injector. All runs were performed at room temperature. Fractions were collected manually or with a PHARMACIA FRAC 100™ collector.

Chromatographic separation performance was evaluated by comparing elution profiles of BSA stock reagent and purified BSA monomer and dimer; the same was done for IgE and the monoclonal antibodies (MAb). Separation of IgE and MAb from their dimers and multimers was further evaluated by analyzing elution fraction using analytical size-exclusion chromatography. Plots of MAb MW forms vs. Fraction number were created. Recovery of IgE and MAb was determined spectrophotometrically by measuring absorbance at 280 nm.

Results

The results are summarized in Table I below.

TABLE I

MONOMER-DIMER/MULTIMER SEPARATIONS

| RESIN | PROTEIN | PH | EQUILIBRATION BUFFER | ELUTION | COMMENTS |
|---|---|---|---|---|---|
| Anion-Exchange | | | | | |
| QSFF ™ | MAb | 8 | Tris-HCl | linear gradient: 0 to 500 mM NaCl | Good separation |
| | | | | linear gradient: 50 to 200 mM NaCl | Best separation |
| | | | | step gradients to 200, 175, 150, 125 mM NaCl | Separation works |
| Resource Q ™ | MAb | 8 | Tris-HCl | | |
| Resource Q ™ | U266 IgE | 8 | Tris-HCl | | Removed aggregates and multimers |
| Resource Q ™ | BSA Monomer | 8 | Tris-HCl | linear gradient: 0 to 1 M NaCl, | Good separation |
| | BSA | | | linear gradients: 150 | Excellent |

TABLE I-continued

MONOMER-DIMER/MULTIMER SEPARATIONS

| RESIN | PROTEIN | PH | EQUILIBRATION BUFFER | ELUTION | COMMENTS |
|---|---|---|---|---|---|
| | Dimer | | | to 550, 250 to 550 mM NaCl | separation |
| | BSA Mix, native | | | | |
| | BSA Mix, blocked | | | step gradients: 0.3/0.6, 0.38/0.6, 0.4 M/0.6 M NaCl | Some separation but fine control required |
| Resource Q ™ | BSA Monomer | 6 | sodium citrate | linear gradient: | Does not bind in citrate pH 6 |
| | BSA Dimer | | | | Does not bind in citrate pH 6 |
| | BSA Mix, blocked | | | | Does not bind in citrate pH 6 |
| Resource Q ™ | BSA Monomer | 6 | sodium phosphate | linear gradient: 0 to 0.5 M NaCl in 10 CVs | good separations |
| | BSA Dimer | | | | |
| | BSA Mix, blocked | | | | |
| Cation Exchange | | | | | |
| Resource S ™ | BSA Monomer | 6 | sodium citrate | linear gradient: 0 to 0.5 M NaCl in 10 CVs | does not bind in citrate pH 6 |
| | BSA Dimer | | | | does not bind in citrate pH 6 |
| | MAb | | | | does not bind in citrate pH 6 |
| Resource S ™ | MAb | 6 | sodium phosphate | linear gradient: 0 to 0.05 M NaCl in 20 CVs | equivalent to Q separation<br><br>loaded to 16.5 mg/mL |
| Resource S ™ | BSA Monomer | 4.6 | NaOAc buffer | linear gradient: 0 to 1 M NaCl/40 CVs | proteins somewhat resolved |
| | BSA Dimer | | | | |
| | BSA Mix, blocked | | | | |
| | BSA Monomer | 4.3 | NaOAc buffer | linear gradient: 0 to 1 M NaCl/20 CVs | better resolution than pH 4.6 |
| | BSA Dimer | | | | |
| | BSA Mix, blocked | | | | |
| JT Baker CSx ™ | BSA Monomer | 4.6 | NaOAc buffer | linear gradient: 0 to 1 M NaCl/12 CVs | proteins somewhat resolved |
| | BSA Dimer | | | | |
| JT Baker CSx ™ | BSA Monomer | 4.3 | NaOAc buffer | linear gradient: 0 to 1 M NaCl/12 CVs | proteins somewhat resolved |
| | BSA Dimer | | | | |

Separations were evaluated using polymeric polystyrene/divinyl benzene resins (RESOURCE Q and S™), a silica-based resin (JT BAKER CSX™), and an agarose-based resin (Q-SEPHAROSE FAST FLOW™; QSFF). While separations were accomplished using any of these resins, separations worked especially well on Q-SEPHAROSE FAST FLOW™, RESOURCE Q™, and RESOURCE S™. The separation of BSA monomer and dimer from both suppliers looked very similar, suggesting the "Sulfhydryl Modified" material from Bayer did not alter the protein such that the species were easier to separate. It can be seen that phosphate buffer at pH 6 worked well, but no protein bound to the cation- or anion-exchange columns when 20 mM citrate buffer at pH 6 was used as equilibration buffer. Citrate buffer would be expected to work for both anion- and cation-exchange at a lower concentration, e.g., about 5 mM.

Figure 1A:
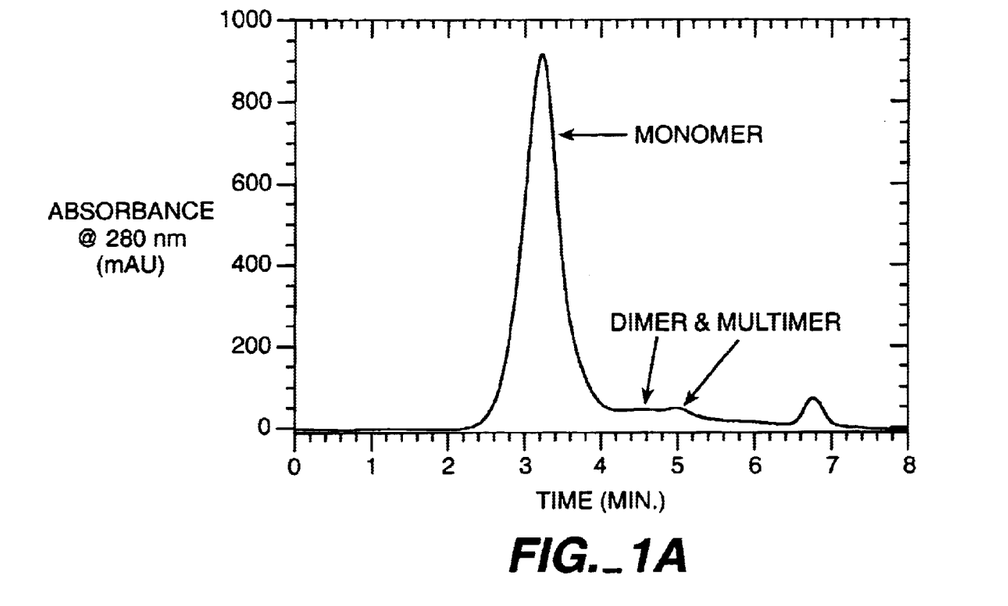
FIGS. 1A and 1B show separation of U266 IgE monomer from dimers and multimers on a RESOURCE Q™ anion-exchange column. The column was equilibrated in 25 mM Tris/pH 8, and eluted with a gradient from 0 to 0.5 M sodium chloride over 10 column volumes.
Figure 1B:
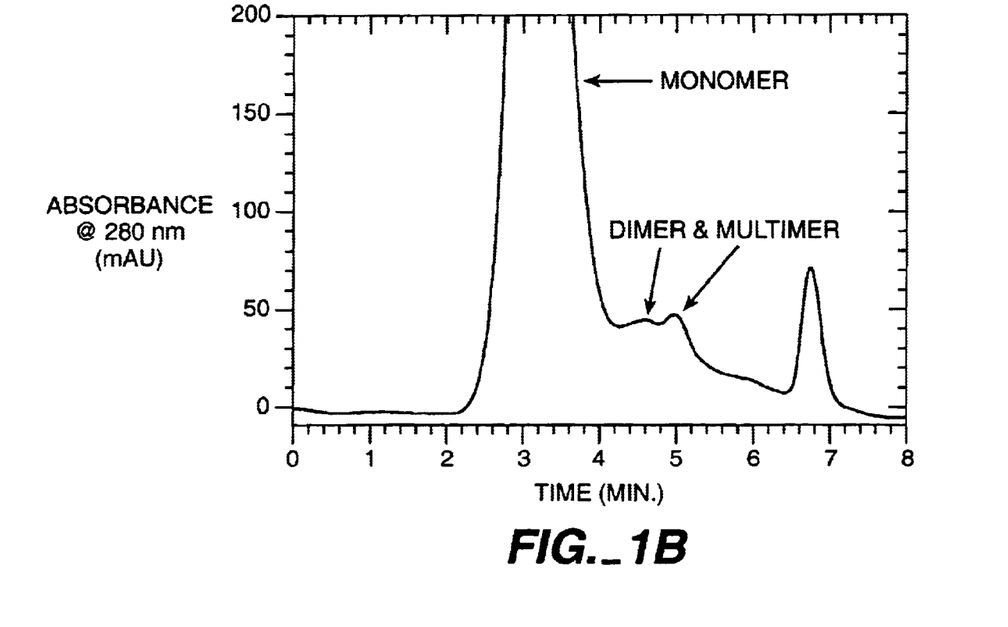
Figure 2A:
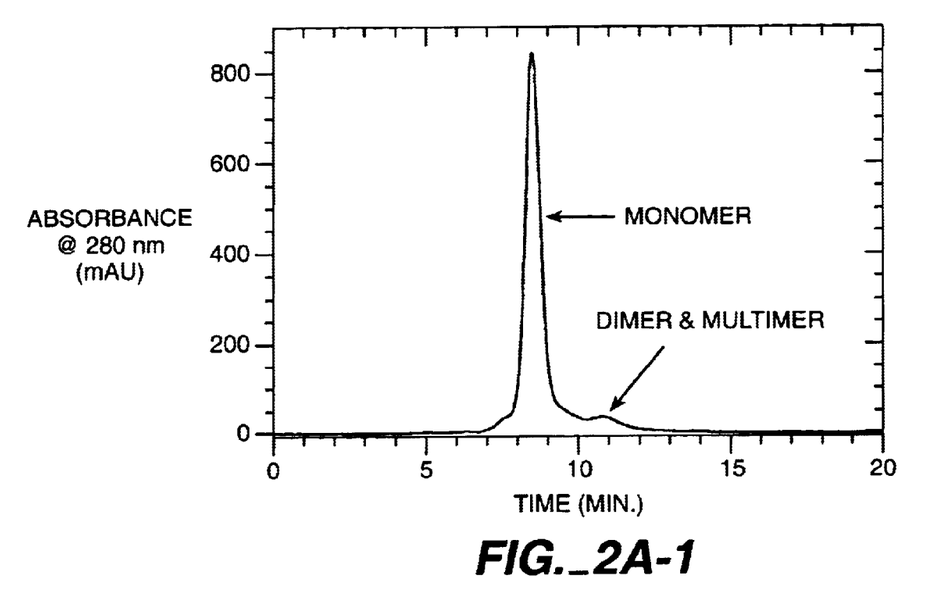
Figure 2A:
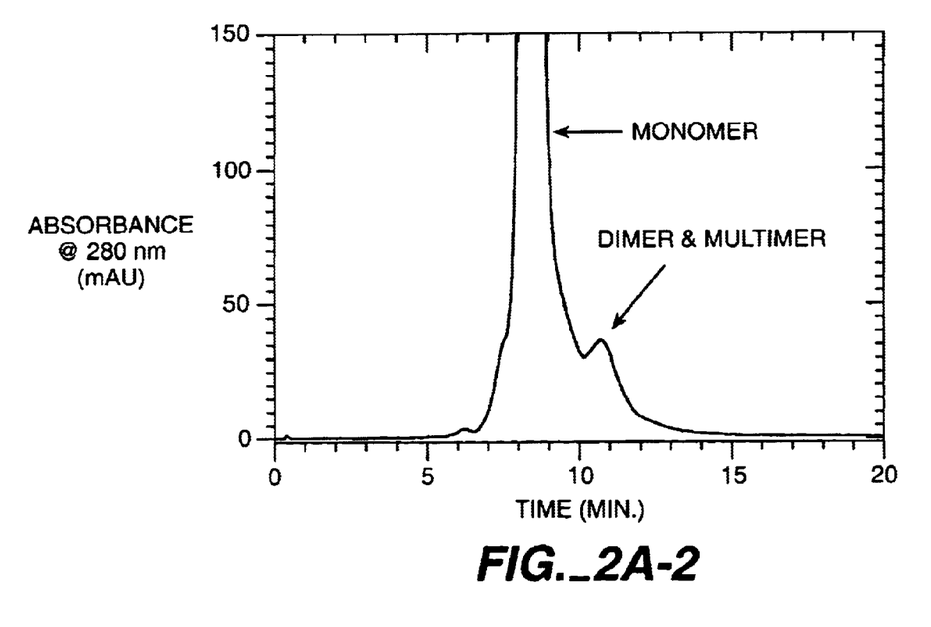
Figure 2B:
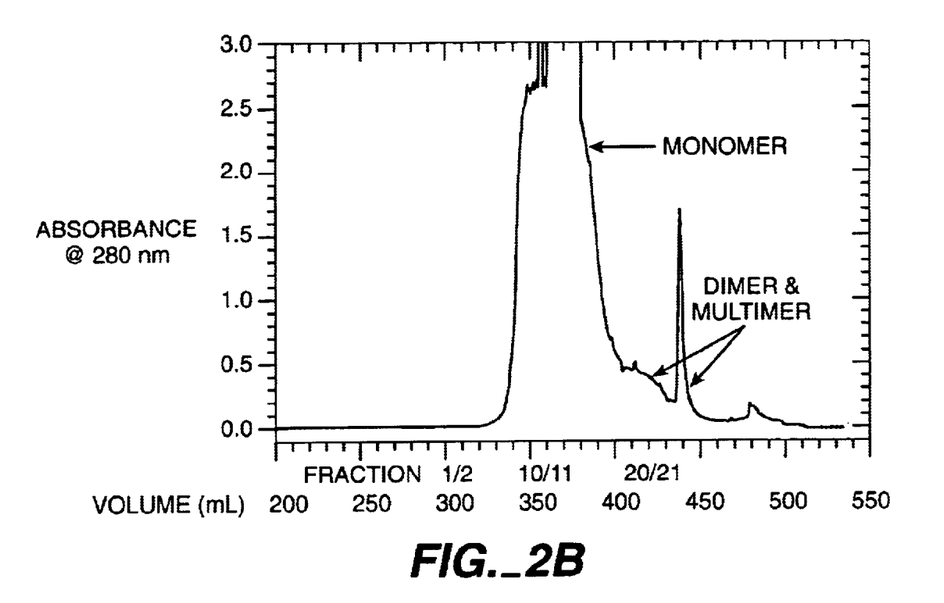
Figure 2C:
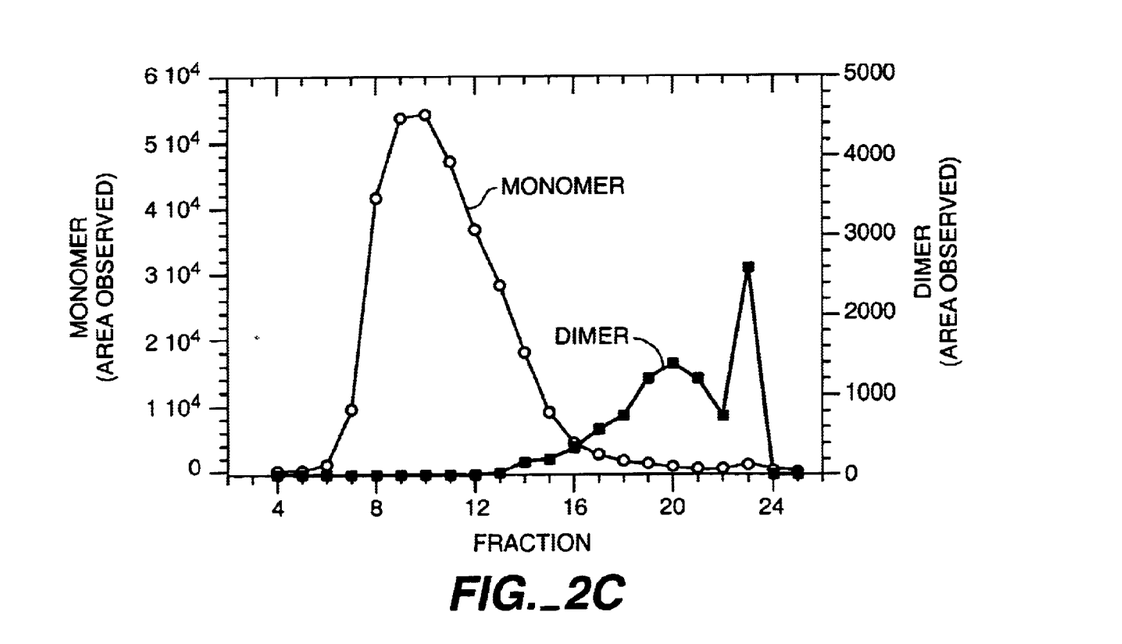
Figure 3A:
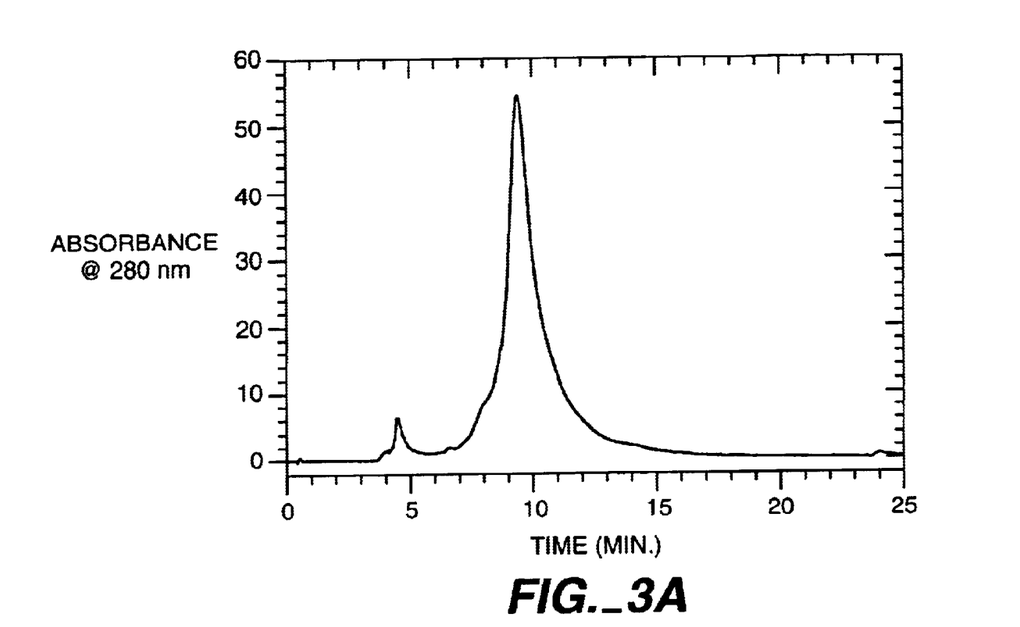
Figure 3B:
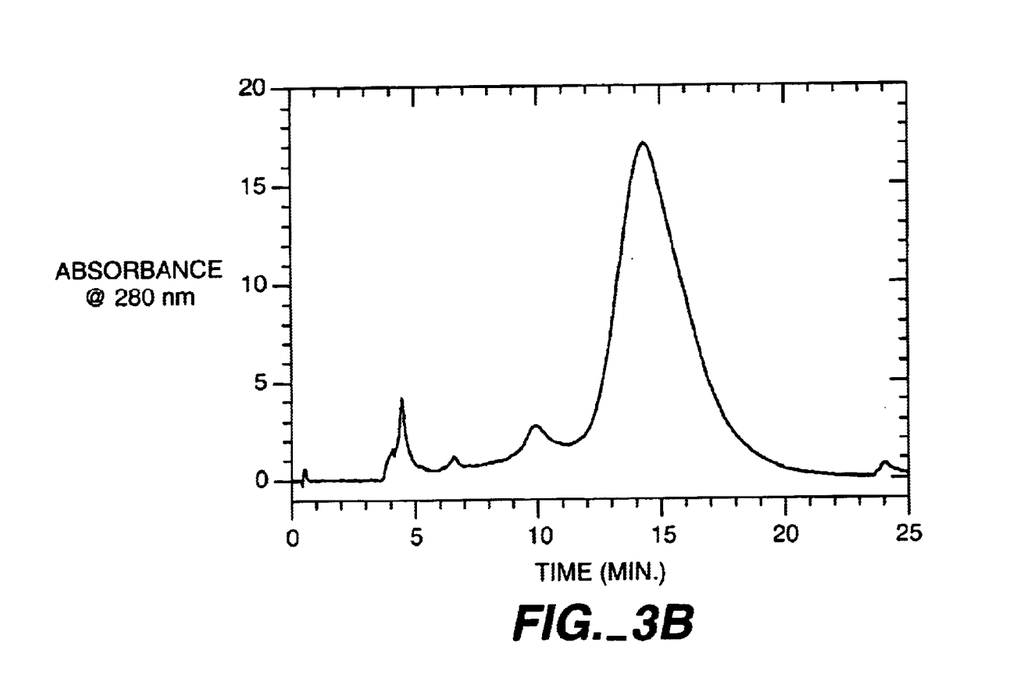
Figure 3C:
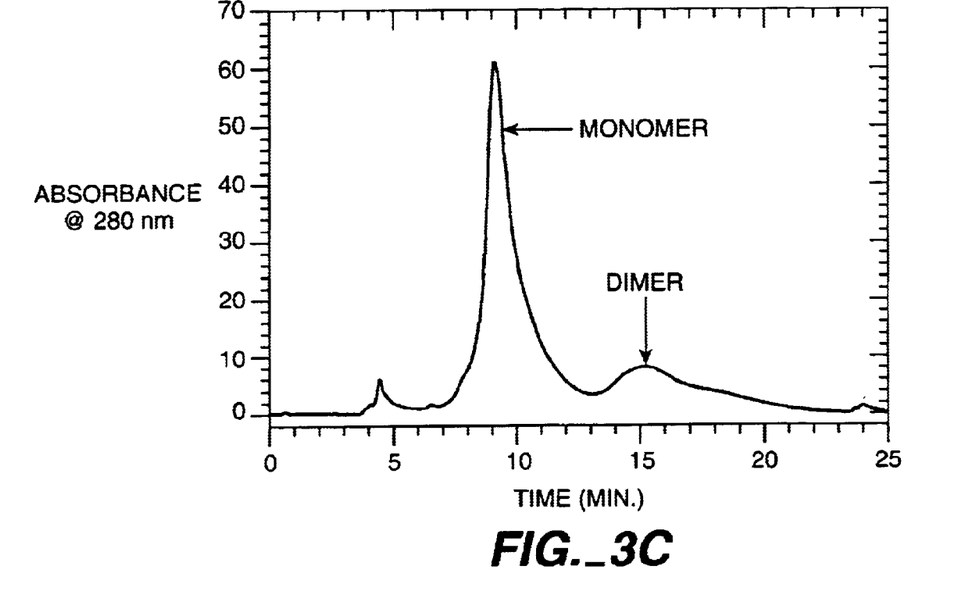
Figure 4A:
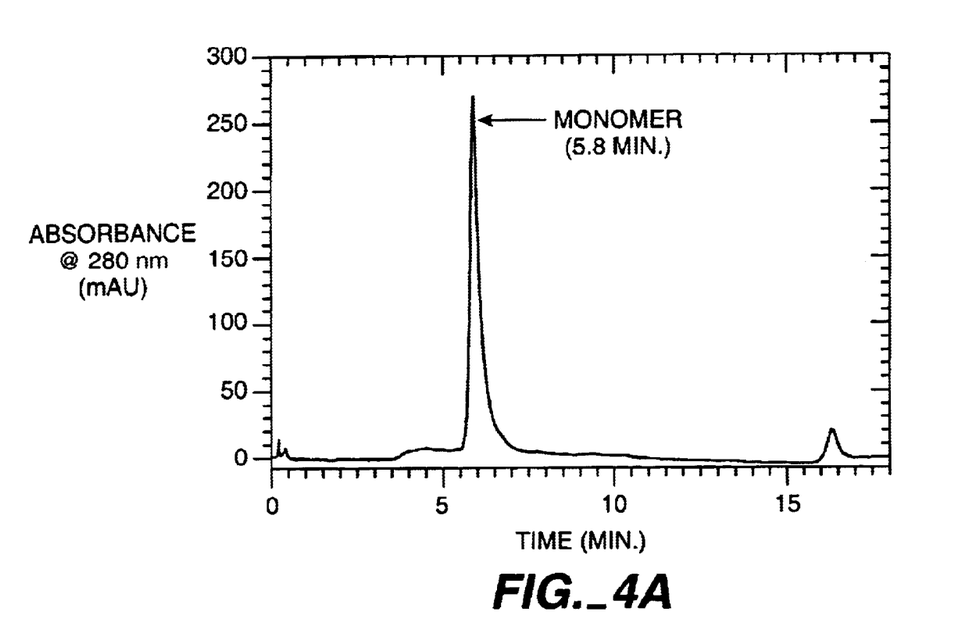
Figure 4B:
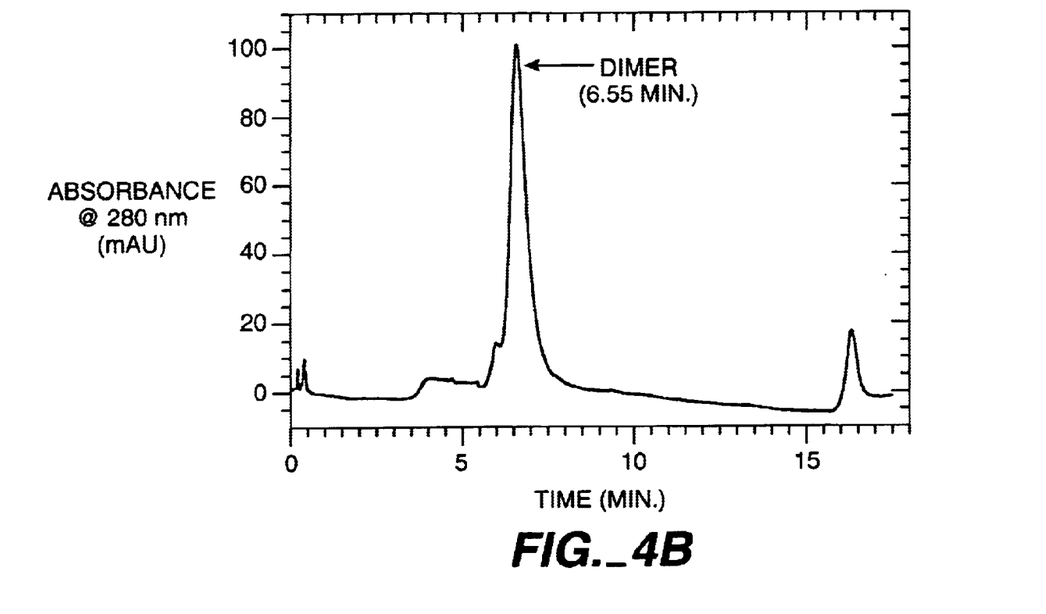
Figure 4C:
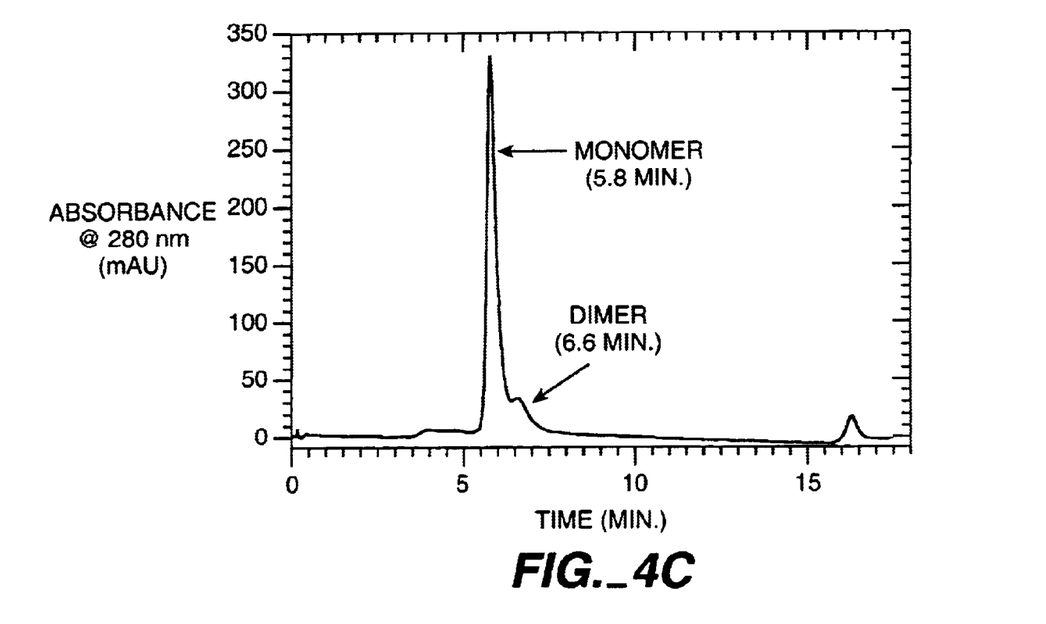

Recovery of monomeric IgE and MAbs to IgE on anion-exchange resins was typically greater than 90% at greater than 99.5% purity. FIGS. 1A and 1B show anion-exchange (RESOURCE™ Q) chromatograms in the separation of IgE monomers from dimers and multimers. FIGS. 2A1 and 2A2 show anion-exchange (RESOURCE™ Q) chromatograms in the separation of anti-IgE MAb monomers from dimers and multimers. FIG. 2B shows an anion-exchange (Q-SEPHAROSE FAST-FLOW™) chromatogram in the separation of anti-IgE MAb monomers from dimers and multimers. SEC (SUPERDEX 200 HR 10/30™) was used as an analytical method to determine the amount of monomer and multimer in samples from the ion-exchange separation, and FIG. 2C shows the SEC analysis of fractions from FIG. 2B. Separation of BSA monomer from dimer was readily achieved on anion-exchange resins at pH 8 and pH 6. See FIGS. 3A–C and 4A–C for chromatograms in the separation of BSA monomers from dimers and multimers by anion-exchange (RESOURCE™ Q) at pH 8 (Tris buffer) and at pH 6 (phosphate buffer), respectively.

Figure 5A:
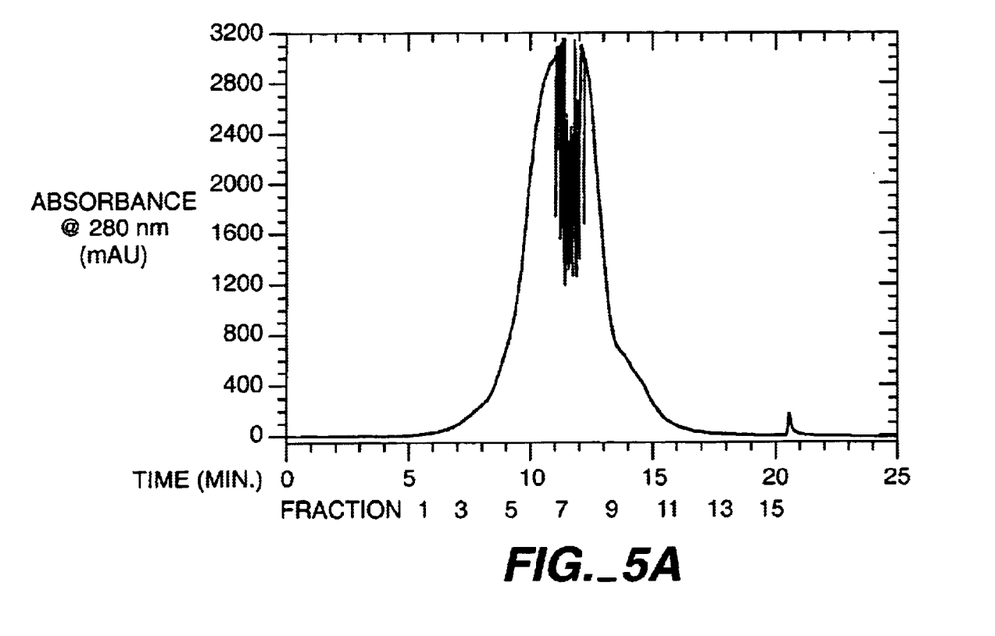
Figure 5B:
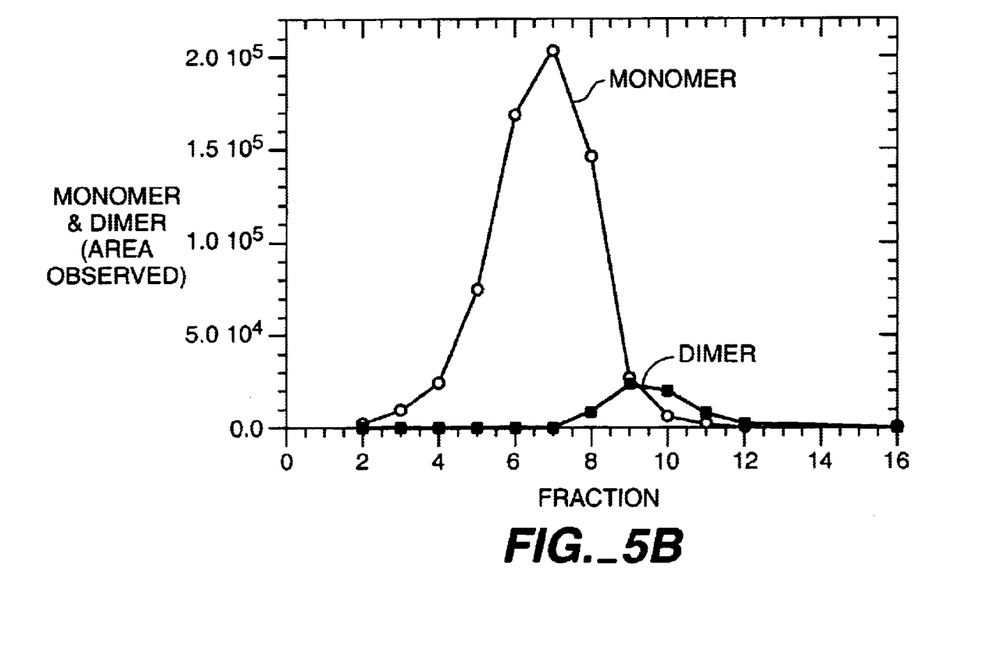
Figure 6A:
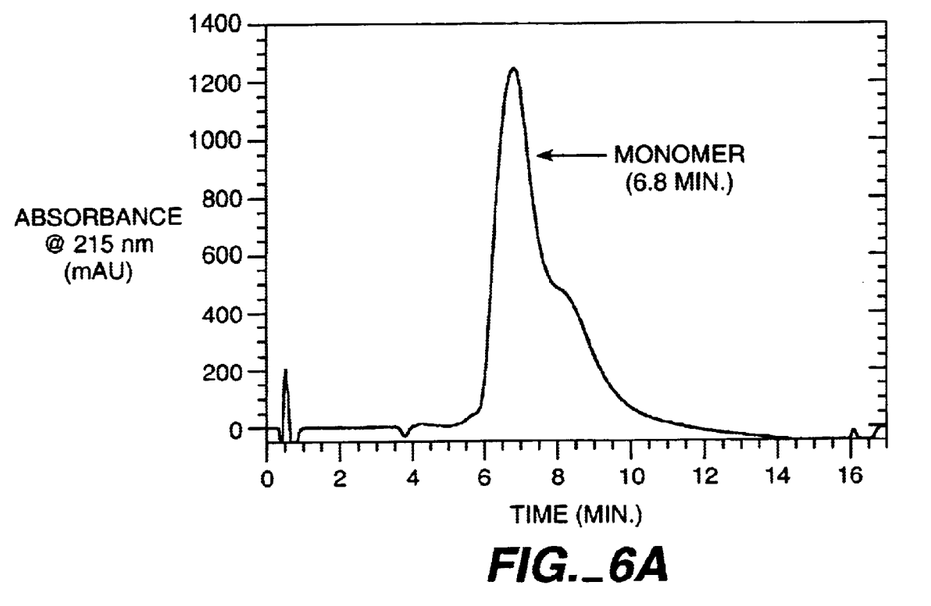
FIGS. 6A and 6B show separation of BSA monomer and dimer on a RESOURCE S™ cation-exchange column at pH 4.3. The column was equilibrated in 20 mM sodium acetate/pH 4.3, then eluted with a gradient from 0 to 1 M sodium chloride over 20 column volumes.
Figure 6B:
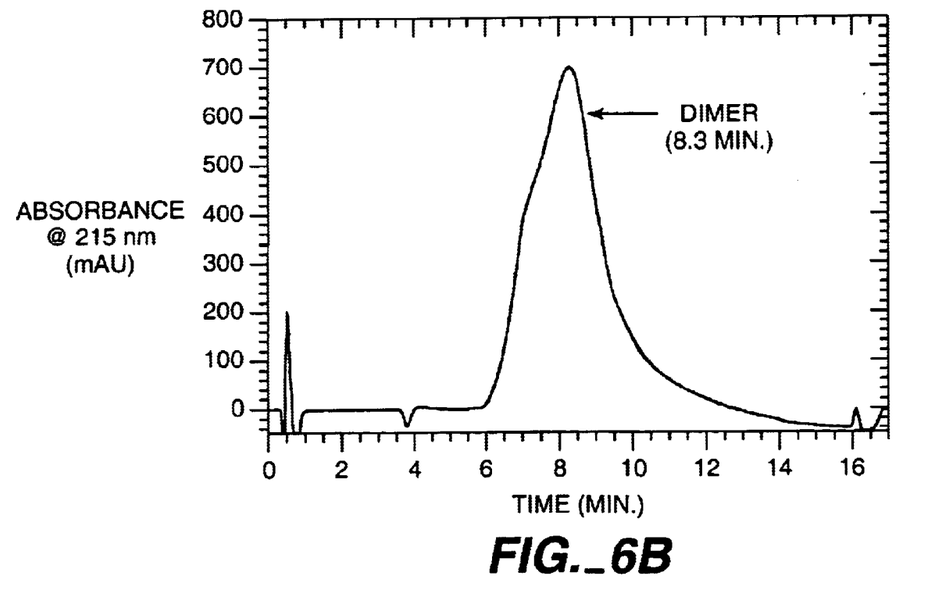

Recovery and purity of MAb monomer from the cation-exchange resin was comparable to that of the anion-exchange resin. FIGS. 5A–B show cation-exchange (RESOURCE™ S) chromatograms in the separation of anti-IgE MAb monomers from dimers and multimers at pH 6 (phosphate buffer). Separations of BSA on cation-exchange resins could be performed at pH 4.6 and 4.3, 4.3 being somewhat better. FIGS. 6A–B show cation-exchange (RESOURCE™ S) chromatograms in the separation of BSA monomers from dimers and multimers at pH 4.3 (acetate buffer).

In summary, mixtures of polypeptide mers were subjected to cation- or anion-exchange chromatography using a variety of resins and under a variety of pH and elution salt conditions, and successful separation was achieved. Based on results from four proteins with basic and acidic isoelectric points (two IgG, MAbs, IgE and serum albumin), the method demonstrates general applicability to separation of polypeptide monomers from their dimers and multimers.

What is claimed is:

1. A method for purifying polypeptide monomers from a mixture consisting essentially of said polypeptide monomers, and dimers or multimers of said polypeptide monomers or both dimers and multimers of said polypeptide monomers, wherein the method consists essentially of applying the mixture to a cation-exchange or anion-exchange chromatography resin in a buffer, wherein if the resin is cation-exchange, the pH of the buffer is about 4–7, and wherein if the resin is anion-exchange, the pH of the buffer is about 6–9, and eluting the mixture at a gradient of about 0–1 M of an elution salt, wherein the monomer is purified from the dimers or multimers or both present in the mixture, and wherein the purified monomer has a purity of greater than 99.5% and the monomer yield is greater than 90%.

2. The method of claim 1 wherein the polypeptide is a serum albumin.

3. The method of claim 1 wherein the polypeptide is anti-IgE, anti-IgG, anti-Her-2, anti-CD11a, anti-CD18, anti-CD20, anti-VEGF, or IgE.

4. The method of claim 2 wherein the serum albumin is bovine serum albumin.

5. The method of claim 1 wherein the ion-exchange resin is a cation-exchange resin.

6. The method of claim 1 wherein the ion-exchange resin is an anion-exchange resin.

7. The method of claim 1 wherein the gradient is linear.

8. The method of claim 1 wherein the gradient is stepwise.

9. The method of claim 1 wherein the elution salt is a sodium salt.

10. The method of claim 9 wherein the elution salt is sodium chloride.

11. The method of claim 1 wherein the gradient is from 0 to 500 mM elution salt.

12. The method of claim 1 wherein the gradient is from 50 to 200 mM elution salt.

13. The method of claim 1 wherein the gradient is from 0 to 50 mM elution salt.

14. The method or claim 1 wherein the polypeptide is an antibody.

15. The method of claim 1 wherein the polypeptide is a monoclonal antibody.

* * * * *

US006620918C1

(12) EX PARTE REEXAMINATION CERTIFICATE (5947th)
United States Patent
Ansaldi et al.

(10) Number: US 6,620,918 C1
(45) Certificate Issued: Oct. 16, 2007

(54) SEPARATION OF POLYPEPTIDE MONOMERS

(75) Inventors: Deborah Ann Ansaldi, San Mateo, CA (US); Philip Lester, San Lorenzo, CA (US)

(73) Assignee: Genentech, Inc., South San Francisco, CA (US)

Reexamination Request:
No. 90/007,835, Dec. 2, 2005

Reexamination Certificate for:
Patent No.: 6,620,918
Issued: Sep. 16, 2003
Appl. No.: 09/320,100
Filed: May 26, 1999

Related U.S. Application Data

(60) Provisional application No. 60/087,602, filed on Jun. 1, 1998.

(51) Int. Cl.
*C07K 1/18* (2006.01)
*C07K 1/00* (2006.01)
*C07K 14/765* (2006.01)
*C07K 16/00* (2006.01)
*C07K 16/42* (2006.01)

(52) U.S. Cl. ............ 530/416; 530/412; 530/413; 530/417; 530/418

(58) Field of Classification Search .................. None
See application file for complete search history.

(56) References Cited

U.S. PATENT DOCUMENTS

| | | | |
|---|---|---|---|
| 4,136,094 A | 1/1979 | Condie | |
| 4,228,154 A | 10/1980 | Fisher et al. | |
| 4,639,513 A | 1/1987 | Hou et al. | |
| 4,736,020 A | 4/1988 | Hillen et al. | |
| 4,764,279 A | 8/1988 | Tayot et al. | |
| 4,765,903 A | 8/1988 | D'Andrea et al. | |
| 5,064,943 A | 11/1991 | McCoy et al. | |
| 5,106,832 A | 4/1992 | Froesch et al. | |
| 5,110,913 A | 5/1992 | Coan et al. | |
| 5,196,323 A | 3/1993 | Bodo et al. | |
| 5,231,178 A | 7/1993 | Holtz et al. | |
| 5,250,662 A | 10/1993 | Chang | |
| 5,250,663 A | 10/1993 | Tenold | |
| 5,256,294 A | 10/1993 | van Reis | |
| 5,490,937 A | 2/1996 | van Reis | |
| 6,177,548 B1 | 1/2001 | Wan et al. | |
| 6,489,447 B1 | 12/2002 | Basey et al. | |

FOREIGN PATENT DOCUMENTS

| | | |
|---|---|---|
| AU | 91328/82 | 8/1983 |
| CA | 1128418 | 7/1982 |
| EP | 373325 | 6/1990 |
| EP | 452753 | 10/1991 |
| EP | 460426 B1 | 9/1997 |
| JP | 1-226827 | 11/1981 |
| JP | 2-222697 | 9/1990 |
| JP | 7-285885 | 10/1995 |
| JP | 8-506247 | 7/1996 |
| WO | 86/06727 | 11/1986 |
| WO | 89/03225 | 8/1989 |
| WO | 91/18621 | 12/1991 |
| WO | WO 92/04970 | 4/1992 |
| WO | 92/13556 | 8/1992 |
| WO | 95/01994 | 1/1995 |
| WO | 96/40776 | 12/1996 |
| WO | 97/45140 | 12/1997 |
| WO | WO 99/57134 | 11/1999 |

OTHER PUBLICATIONS

Gooding, K.M. and Schmuck, M.N. Journal of Chromatography, 327: 139–146, 1985.*
Jiskoot et al., Symposium on Monoclonal antibodies for Therapy, Prevention and in vivo Diagnosis of Human Disease, Utrecht, The Netherlands, 1989; *Develop. Biol. Standard.* 71:73–78, 1990.
Aoyama and Chiba, *J. Immunol. Methods* 162:201–210, 1993.
Scopes, *Protein Purification: Principles and Practice*, 2nd. Ed. Charles Cantor ed., Springer–Verlag New York, 1987, Chapter 5.
Lemque et al., *J. Chromatograhy* 599:255–265, 1992.
Lynch and Londo, *Genetic Engineering News*, Nov. 1, 1997 (Lynch).
Duffy et al., Biopharma, 1989 pp. 34–44, 47.
Arndt, et al., Biochemistry 37: 12918, 1998.
Alberts et al. (Molecular Biology of the Cell (1983), p. 121–122).
Lewin (Genes IV (1990), p. 14.
Bjork, Ingemar et al., "Gross Conformation of Human Secretory Immunoglobulin A and Its Component Parts" *European Journal of Biochemistry* 45:134–145 (1974).
Bruck et al., "Purification of mouse monoclonal antibodies from ascitic fluid by DEAE Affi–Gel Blue chromatography" *Methods in Enzymology* 121:587–596 (1986).
Chang et al., "Single–Step Solubilization and Folding of YGF–1 Aggregates from *Escherichia coli*" *Protein Folding: In Vivo and In Vitro*, American Chemical Society, Chapter 14, pp. 178–188 (1993).
Chaudhary, V. K., et al., "A recombinant immunotoxin consisting of two antibody variable domains fused to *Pseudomonas exotoxin*" Nature 339:394–397 (Jun. 1, 1989).
Chicz et al., "Surface–Mediated Retention Effects of Subtilisin Site–Specific Variants in Cation–Exchange Chromatography" *Journal of Chromatography* 443:193–203 (1988).
"Choice of exchanger group" *Ion Exchange Chromatography Principles and Methods* pp. 51 (1994).
Coleman et al. *Journal of Biological Chemistry* 270(23):13842–13849 (1995).

(Continued)

*Primary Examiner*—S. L. Turner (57) ABSTRACT

A method is disclosed for separating a polypeptide monomer from a mixture comprising dimers and/or multimers. The method comprises applying the mixture to either a cation-exchange chromatography resin or an anion-exchange chromatography resin and eluting the mixture at a gradient of about 0–1 M of an elution salt, wherein the monomer is separated from the dimers and/or multimers present in the mixture.

OTHER PUBLICATIONS

Crimmins, "Analysis of Disulfide–Linked Homo– and hetero–Peptide Dimers with a Strong Cation–Exchange Sulfoethyl Aspartamide Column" *Peptide Research* 2(6):395–401 (1989).

Database WPI Week 9601 AN 96–006908 & JP 07 285885 A (English abstract of Reference 34 hereof), London:Derwent Publications Ltd.

De Rie, Menno A., et al., "Evaluation of a method of production and purification of monoclonal antibodies for clinical applications" *J. of Immunological Methods* 102:187–193 (1987).

Elliott et al., "Yeast–Derived Recombinant Human Insulin–Like Growth Factor I: Production, Purification, and Structural Characterization" *J. Protein Chem.* 9(1):95–104 (1990).

Gagnon, Pete, "Ion Exchange Chromatography" *Purification Tools for Monoclonal Antibodies*, Chapter 4, pp. 57–86 (1996).

Gemski et al. *Biotechniques* 3(5):378–384 (1985).

Graf et al., "Ion exchange resins for the purification of monoclonal antibodies from animal cell culture" *Bioseparation* 4(1):7–20 (Feb. 1994).

Gupta et al., "Protein Aggregation kinetics: Applications to protein A chromatography" *CAPLUS, Bibliography & Abstract, fur:* (Abstract Nr. 2003:179302; Paper abstract ACS National meeting, new Orleans, LA, U.S.A.) (Mar. 23–27, 2003).

Haase–Pettingell and King *Journal of Biological Chemistry* 263(10):4977–4983 (1988).

Hahn et al., "Bovine whey fractionation based on cation–exchange chromatography" *J. of Chromatography* 795:277–287 (Feb. 1998).

Harlow et al., "Antibody Molecules" *Antibodies: A Laboratory Manual*, Cold Spring Harbor Laboratory pp. 7, 10 (1988).

Higo et al., "Model study of 2–dim. protein aggregates in the nucleation stage of crystallization" *J. Chem. Phys.* 99:9156–9162 (1993).

Hoogewerf et al., "CXC Chemokines Connective Tissue Activating Peptide–III and Neutrophil Activating Peptide–2 are Heparin/Heparan Sulfate–degrading Enzymes" *Journal of Biological Chemistry* 7:3268–3277 (1995).

Jiskoot, W., et al., "Two–step purification of a murine monoclonal antibody intended for therapeutic application in man—Optimisation of purification conditions and scaling up" *J. of Immunological Methods* 124:143–156 (1989).

Karlsson and Ryden, "Ion–Exchange Chromatography" *Protein Purification: Principles, High Resolution Methods, and Applications second edition*, John Wiley & Sons pp. 145–160 & 200–205 (1998).

Karlsson, Evert; Ryden, Lars, "Ion–Exchange Chromatography" *Protein Purification—Principles, High–Resolution Methods and Applications*, Jan–Christer Janson and Lars Ryden, Second edition, John Wiley & Sons pp. 145–205 (1998).

Li, F., et al. www.bioprocessingjournal.com, Sep./Oct. edition 4(5):1–8, 23 (2005).

Mann et al., "3.7–3.7.4" *Natural Products: their chemistry and biological significance*, first edition, Longman Scientific & Technical pp. 194–199 (1994).

Mateu and Fersht *EMBO H*, 17(10):2748–2758 (1998).

Noeva et al., "Antigenicity of Aggregated Immunoglobulins in Gamma Globulin Preparations" *Comptes rendus de l'Academie bulgare des Sciences* 27(9):1291–1294 (1974).

Patro et al., "Simulations of Reversible Protein Aggregate and Crystal Structure" *Biophysical J.* 70:2888–2902 (1996).

*Protein Purification Methods, a practical approach* (ISBN: 0 19 963003 8), Harris ELV and Angal S., Oxford University Press pp. 175–244 (1995).

Roitt, "Molecules Which Recognize Antigen" *Essential Immunology*, Sixth edition, Blackwell Scientific Publications pp. 31, 40 (1988).

Tankersley D.L. et al. *Mol. Immuno.* 25(1):41–48 (1988).

Teeling et al., "Therapeutic efficacy of intravenous immunoglobulin preparations depends on the immunoglobulin G dimers: studies in experimental thrombocytopenia" *Immunobiology* 98(4):1095–1099 (2001).

Voet, Donald und Judith G. *Biochemistry*, John Wiley & Sons, Inc. pp. 1099–1100 (1990).

Whitlow et al., "Multivalent Fvs: characteization of single–chain Fv oligomers and preparation of bispecific Fv" *Protein Engineering* 7(8):1017–1026 (1994).

Yang et al., "Influence of column type and chromatographic conditions on the ion exchange chromatography of immunoglobulins" *J. of Chromatography* 743:171–180 (1996).

Yang, J., et al., "A Genetically Engineered Single–Chain FV/TNF Molecule Possesses the Anti–Tumor Immunoreactivity of FV as well as the Cytotoxic Activity of Tumor Necrosis Factor" *Molecular Immunology* 32(12):873–881 (1995).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2–4 and 14–15 are cancelled.

Claim 1 is determined to be patentable as amended.

Claims 5–13, dependent on an amended claim, are determined to be patentable.

1. A method for purifying polypeptide monomers from a mixture consisting essentially of said polypeptide monomers, and dimers or multimers of said polypeptide monomers or both dimers and multimers of said polypeptide monomers, wherein the method consists essentially of applying the mixture to a cation-exchange or anion-exchange chromatography resin in a buffer, wherein if the resin is cation-exchange, the pH of the buffer is about 4–7, and wherein if the resin is anion-exchange, the pH of the buffer is about 6–9, and eluting the mixture at a gradient of about 0–1 M of an elution salt, wherein the monomer is purified from the dimers or multimers or both present in the mixture, and wherein the purified monomer has a purity of greater than 99.5% and the monomer yield is greater than 90%, *wherein the polypeptide is anti-IgE, anti-IgG, anti-Her-2, anti-CD11a, anti-CD18, anti-CD20, anti-VEGF, or IgE.*

* * * * *